(12) United States Patent
Holoshitz et al.

(10) Patent No.: US 10,494,405 B2
(45) Date of Patent: Dec. 3, 2019

(54) METHODS AND COMPOSITIONS FOR THE TREATMENT OF ARTHRITIS

(71) Applicant: THE REGENTS OF THE UNIVERSITY OF MICHIGAN, Ann Arbor, MI (US)

(72) Inventors: Joseph Holoshitz, Ann Arbor, MI (US); Katarzyna Sobczyk-Kojiro, Ann Arbor, MI (US); Song Ling, Ypsilanti, MI (US); Henry I. Mosberg, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/573,962

(22) PCT Filed: May 13, 2016

(86) PCT No.: PCT/US2016/032374
§ 371 (c)(1),
(2) Date: Nov. 14, 2017

(87) PCT Pub. No.: WO2016/187013
PCT Pub. Date: Nov. 24, 2016

(65) Prior Publication Data
US 2018/0291064 A1    Oct. 11, 2018

Related U.S. Application Data

(60) Provisional application No. 62/162,350, filed on May 15, 2015.

(51) Int. Cl.
*A61K 38/08*    (2019.01)
*A61K 38/12*    (2006.01)
(Continued)

(52) U.S. Cl.
CPC .............. *C07K 9/001* (2013.01); *A61K 38/08* (2013.01); *A61K 38/12* (2013.01); *A61K 38/14* (2013.01);
(Continued)

(58) Field of Classification Search
CPC .......... A61K 38/08; A61K 38/12; C07K 7/06; C07K 7/50; C07K 7/54; C07K 7/56; C07K 7/64
See application file for complete search history.

(56) References Cited

U.S. PATENT DOCUMENTS

| 5,616,556 A | 4/1997 | Fujii et al. |
| 7,074,893 B2 | 7/2006 | Holoshitz et al. |
| 7,208,154 B2 | 4/2007 | Holoshitz et al. |

FOREIGN PATENT DOCUMENTS

| CN | 102229657 A | 11/2011 |
| WO | 2005/111225 | 11/2005 |

(Continued)

OTHER PUBLICATIONS

Bromley et al., "Chondroclasts and Osteoclasts at Subchondral Sites of Erosion in the Rheumatoid Joint" 1984 Arthritis Rheum. 27(9): 968-975.

(Continued)

*Primary Examiner* — Jeffrey E. Russel
(74) *Attorney, Agent, or Firm* — Casimir Jones, S.C.; Tanya Arenson

(57) ABSTRACT

The present disclosure relates to methods and compositions for treating disease related to disorders of bone remodeling. In particular, the present disclosure relates to cyclic peptide compositions and methods for treating rheumatoid arthritis.

15 Claims, 3 Drawing Sheets

Specification includes a Sequence Listing.

BK2
Trp-c[Gly(4-aminobutyl)-Asp-Lys-Ser-Gly(4-aminobutyl)]-Ala-NH2

(51) Int. Cl.
    *C07K 7/06* (2006.01)
    *C07K 7/56* (2006.01)
    *C07K 9/00* (2006.01)
    *A61K 38/14* (2006.01)
    *A61P 19/02* (2006.01)
    *A61K 38/00* (2006.01)

(52) U.S. Cl.
    CPC ............... *A61P 19/02* (2018.01); *C07K 7/06* (2013.01); *C07K 7/56* (2013.01); *A61K 38/00* (2013.01)

(56) References Cited

FOREIGN PATENT DOCUMENTS

| WO | 2014/130949 | 8/2014 |
|---|---|---|
| WO | 2014/176604 | 10/2014 |

OTHER PUBLICATIONS

De Almeida et al., "Immune Dysregulation by the Rheumatoid Arthritis Shared Epitope" 2010. The Journal of Immunology 185: 1927-1934.
Filip et al., "Potent side-chain to side-chain cyclized dermorphin analogues containing a carbonyl bridge." Journal of Peptide Science. 9: 649-657, 2003.
Gonzalez-Gay et al., "Influence of human leukocyte antigen-DRB1 on the susceptibility and severity of rheumatoid arthritis" 2002. Semin. Arthritis Rheum. 31: 355-360.
Gravallese et al., "Synovial tissue in rheumatoid arthritis is a source of osteoclast differentiation factor." 2000. Arthritis Rheum. 43: 250-258.
Gregersen et al., "The shared epitope hypothesis. An approach to understanding the molecular genetics of susceptibility to rheumatoid arthritis." 1987. Arthritis Rheum. 30: 1205-1213.
Holoshitz et al., "A role for calreticulin in the pathogenesis of rheumatoid arthritis" 2010 Ann. N. Y. Acad. Sci. 1209: 91-98.
International Search Report and Written Opinion, International Patent Application No. PCT/US2016/032374, dated Aug. 25, 2016, 12 pages.
Jawaheer et al., ""Homozygosity" For the HLA-DR Shared Epitope Contributes the Highest Risk for Rheumatoid Arthritis Concordance in Identical Twins" 1994 Arthritis Rheum. 37: 681-686.
Kotake et al., "IL-17 in synovial fluids from patients with rheumatoid arthritis is a potent stimulator of osteoclastogenesis." 1999 J. Clin. Invest. 103: 1345-1352.
Ling et al., "Activation of nitric oxide signaling by the rheumatoid arthritis shared epitope" 2006. Arthritis Rheum. 54: 3423-3432.
Ling et al.,"The rheumatoid arthritis shared epitope increases cellular susceptibility to oxidative stress by antagonizing an adenosine-mediated anti-oxidative pathway" 2007. Arthritis Res Ther 9: R5.
Ling et al., "The Rheumatoid Arthritis Shared Epitope Triggers Innate Immune Signaling via Cell Surface Calreticulin" 2007. The Journal of Immunology 179: 6359-6367.
Mattey et al., "Independent association of rheumatoid factor and the HLA-DRB1 shared epitope with radiographic outcome in rheumatoid arthritis" 2001. Arthritis Rheum. 44: 1529-1533.
Naveh et al. "Developing Potent Backbone Cyclic Peptides Bearing the Shared Epitope Sequence as Rheumatoid Arthritis Drug-Leads" Bioorganice & Medicinal Chemistry Letters Nov. 4, 2011, vol. 22, p. 493-496.
Plant et al., "Patterns of radiological progression in early rheumatoid arthritis: results of an 8 year prospective study." 1998 J. Rheumatol. 25: 417-426.
Sato et al., "Th17 functions as an osteoclastogenic helper T cell subset that links T cell activation and bone destruction." 2006 J. Exp. Med. 203: 2673-2682.
Shahrara et al., "TH-17 cells in rheumatoid arthritis." 2008 Arthritis Res Ther 10: R93.
Weyand et al., "Disease mechanisms in rheumatoid arthritis: Gene dosage effect of HLA-DR haplotypes" 1994. J. Lab. Clin. Med. 124: 335-338.
Ling et al., "Shared epitope-antagonistic ligands: a new therapeutic strategy in mice with erosive arthritis." Arthritis Rheumatol. May 2015;67(8):2061-70.
Search Report for related 16797009.4, dated Jan. 18, 2019, 8 pages.

BK2

Trp-c[Gly(4-aminobutyl)-Asp-Lys-Ser-Gly(4-aminobutyl)]-Ala-NH2

E

F

METHODS AND COMPOSITIONS FOR THE TREATMENT OF ARTHRITIS

CROSS REFERENCE TO RELATED APPLICATIONS

This application is a 371 U.S. National Phase Entry of pending International Application No. PCT/US2016/032374, filed May 13, 2016, which claims the benefit of U.S. provisional application Ser. No. 62/162,350, filed May 15, 2015, which are incorporated herein by reference in their entireties.

STATEMENT REGARDING FEDERALLY SPONSORED RESEARCH OR DEVELOPMENT

This invention was made with government support under RR024986 and AR059085 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 535 bytes ASCII (Text) file named "34429-US-2-PCT_Replacement_ST25.txt." created on Jun. 19, 2019.

FIELD OF THE DISCLOSURE

The present disclosure relates to methods and compositions for treating disease related to disorders of bone remodeling. In particular, the present disclosure relates to compositions and methods for treating rheumatoid arthritis.

BACKGROUND

Rheumatoid arthritis (RA) is a chronic, systemic inflammatory disorder that may affect many tissues and organs, but principally attacks flexible (synovial) joints. It can be a disabling and painful condition, which can lead to substantial loss of functioning and mobility if not adequately treated.

The process involves an inflammatory response of the capsule around the joints (synovium) secondary to swelling (hyperplasia) of synovial cells, excess synovial fluid, and the development of fibrous tissue (pannus) in the synovium. The pathology of the disease process often leads to the destruction of articular bone and cartilage, and ankylosis (fusion) of the joints. Rheumatoid arthritis can also produce diffuse inflammation in the lungs, membrane around the heart (pericardium), the membranes of the lung (pleura), and white of the eye (sclera), and also nodular lesions, most common insubcutaneous tissue.

Although the cause of rheumatoid arthritis is unknown, autoimmunity plays a pivotal role in both its chronicity and progression, and RA is considered a systemic autoimmune disease. It is a clinical diagnosis made on the basis of symptoms, physical exam, radiographs (X-rays) and labs.

Various treatments are available. Non-pharmacological treatment includes physical therapy, orthoses, occupational therapy and nutritional therapy but these do not stop the progression of joint destruction. Analgesia (painkillers) and anti-inflammatory drugs, including steroids, are used to suppress the symptoms, while disease-modifying antirheumatic drugs (DMARDs) are required to inhibit or halt the underlying immune process and prevent long-term damage. In recent times, the newer group of biologics has increased treatment options. About 1% of the world's population has rheumatoid arthritis, women three times as often as men. Onset is most frequent between the ages of 40 and 50, but people of any age can be affected.

Additional treatments are needed.

SUMMARY OF THE DISCLOSURE

The present disclosure relates to methods and compositions for treating disease related to disorders of bone remodeling. In particular, the present disclosure relates to compositions and methods for treating rheumatoid arthritis.

Embodiments of the present disclosure provide a composition comprising a compound having the structure:

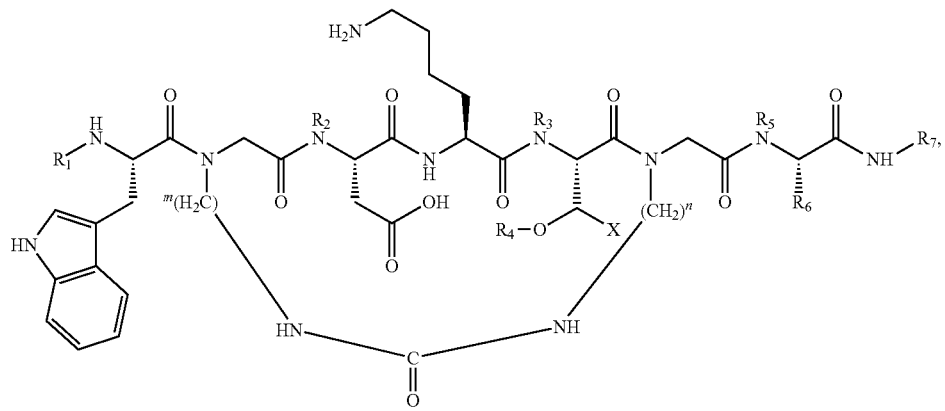

where m and n are the same or different and are integers between 1 and 4; X is H or $CH_3$; $R_1$ is H amidino, a glycosylated serine or threonine residue, or one or more arginine residues, $R_2$ is H or methyl, $R_3$ is H or methyl, $R_4$ is H or a β or α sugar (e.g., glucose, xylose, fucose, lactose, maltose, etc.), $R_5$ is H or methyl, $R_6$ is $CH_3$, OH, or O-β or α sugar (e.g., glucose, xylose, fucose, lactose, maltose, etc.), $R_7$ is H, a glycosylated serine or threonine residue, or one or more arginine residues.

(SEQ ID NO: 1)

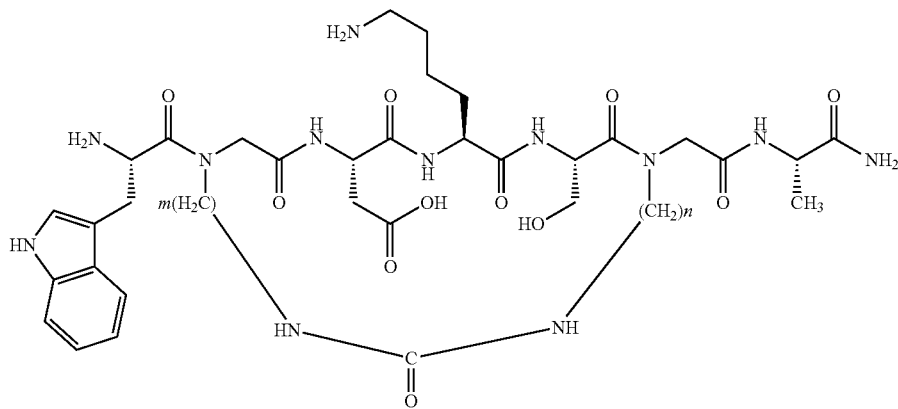

where m and n are integers between 1 and 4. In some embodiments, the structure is:

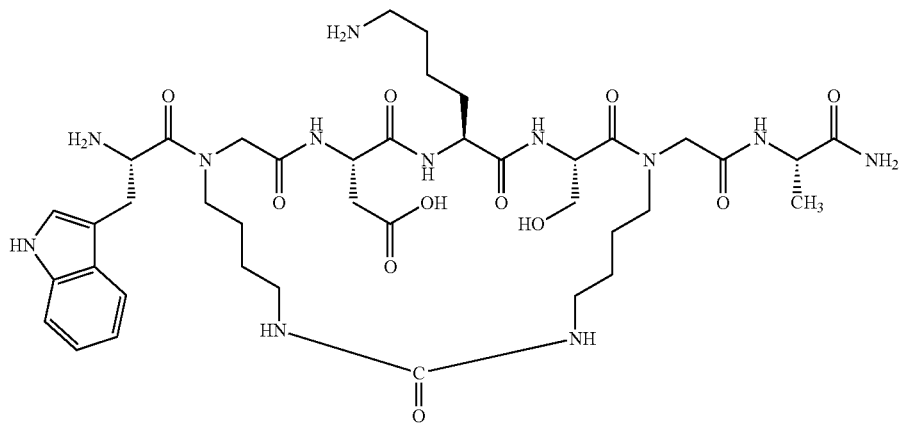 [SMILES: C[C@H](NC(=O)CN1CCCCNC(=O)NCCCCN(C(=O)[C@@H](N)Cc2c[nH]c3ccccc23)CC(=O)N[C@@H](CC(=O)O)C(=O)N[C@@H](CCCCN)C(=O)N[C@@H](CO)C1=O)C(N)=O]

(Trp-c[Gly(4-aminobutyl)-Asp-Lys-Ser-Gly(4-aminobutyl)]-Ala-NH2 (SEQ ID NO:1); FIG. 1).

In some embodiments, the structure is

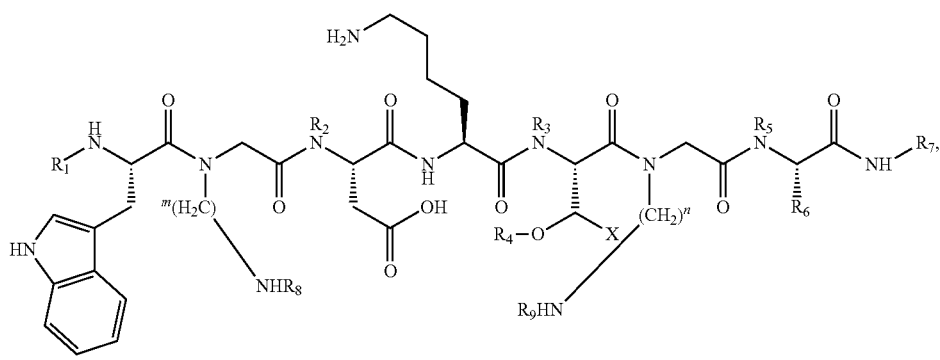

where m and n are the same or different and are integers between 1 and 4; X is H or $CH_3$; $R_1$ is H amidino, a glycosylated serine or threonine residue, or one or more arginine residues, $R_2$ is H or methyl, $R_3$ is H or methyl, $R_4$ is H or a β or α sugar (e.g., glucose, xylose, fucose, lactose, maltose, etc.), $R_5$ is H or methyl, $R_6$ is $CH_3$, OH, or O-β or α sugar (e.g., glucose, xylose, fucose, lactose, maltose, etc.), $R_7$ is H, a glycosylated serine or threonine residue, or one or more arginine residues, $R_8$ is H or acetyl, and $R_9$ is H or acetyl.

In some embodiments, the β-hydroxyl of serine at position 5 is glycosylated. In some embodiments, the c-terminal alanine of the composition is replaced with glycosylated serine. The present disclosure is not limited to particular glycosylation moieties or patterns. In some embodiments, the glycosylation comprises a mono or disaccharide (e.g., β-glucose). In some embodiments, one or more (e.g., 1, 2, 3, 4, or 5) amino acids of the composition are N-methylated (e.g. at one or more of positions 1, 3, 4, 5, or 7). In some embodiments, the N-terminal tryptophan amino acid of the composition is amidinated at the —NH$_2$ group. In some embodiments, the composition is a pharmaceutical composition (e.g., comprising a pharmaceutically acceptable carrier).

Further embodiments provide any of the aforementioned compositions for use in the treatment or prevention of bone remodeling disorder (e.g., bone destruction from rheumatoid arthritis). In some embodiments, the composition prevents or treats bone destruction.

Additional embodiments provide the use of any of the aforementioned compositions for the manufacture of a medicament for treating a bone remodeling disorder.

Further embodiments provide the use of any of the aforementioned compositions for treating a bone remodeling disorder.

Other embodiments provide a method of treating or preventing a bone remodeling disorder, comprising administering any of the aforementioned compositions to a subject. In some embodiments, the subject has been diagnosed with a bone remodeling disorder (e.g., bone destruction from rheumatoid arthritis). In some embodiments, the administration treats or prevents bone destruction.

Additional embodiments are described herein.

DEFINITIONS

Figure 1:
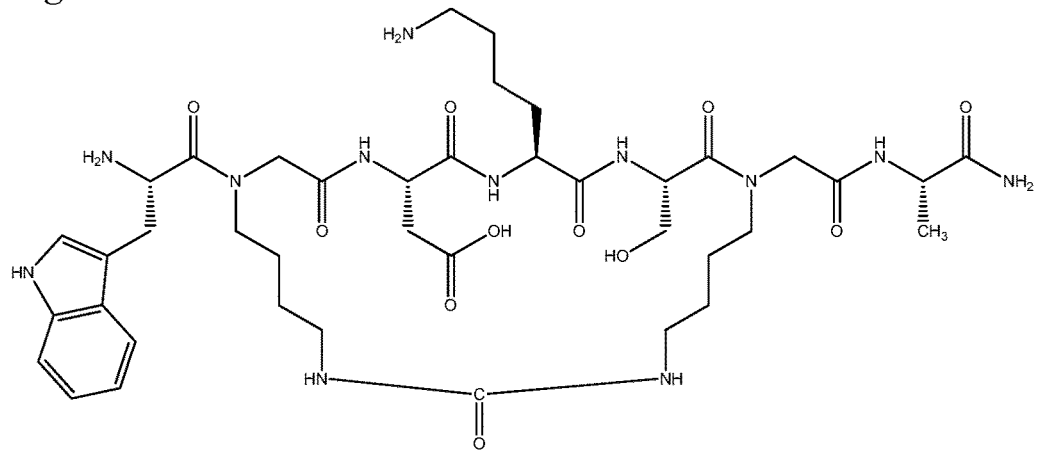
FIG. 1 shows the structure of exemplary compound BK2 (SEQ ID NO:1).

As used herein, the term "disorders of bone remodeling" refers to any disease or disorder that has as a symptom or sign, a disorder or deregulation of bone remodeling. Bone remodeling (or bone metabolism) is a lifelong process where mature bone tissue is removed from the skeleton (a process called bone resorption) and new bone tissue is formed (a process called ossification or new bone formation). An imbalance in the regulation of bone remodeling's two subprocesses, bone resorption and bone formation, results in or is the result of a variety of disorders of, inflammatory, metabolic, pharmacologic endocrinologic, infectious, neopleastic, mecahnical and idiopathic nature. Specific examples of disease related to bone remodeling include, but are not limited to, arthritis (e.g., rheumatoid arthritis), periodontal disease, psoriatic arthritis, reactive arthritis, gout, ankylosing spondylitis, osteoarthritis, osteoporosis, anorexia nervosa, vitamin D deficiency, Cushing's syndrome, hyperparathyroidism, corticosteroids, other drug-induced osteoporosis, osteomyelitis, bone metastasis, primary bone tumors, multiple myeloma, bone fracture healing, post-surgical, prosthesis-associated bone damage, disuse, paralysis, bedridden conditions, low gravity, Paget's disease of bone, and osteonecrosis.

As used herein, "one or more signs or symptoms of rheumatoid arthritis" (RA; rheumatoid arthritis) include tender, warm, swollen joints, usually affected in a symmetrical pattern. Other symptoms of RA include fatigue and occasional fever or malaise. Pain and stiffness lasting more than 30 minutes in the morning or after a long rest are also common symptoms of RA.

As used herein, "improved" means a reduction in the severity of the signs or symptoms of a disease (e.g., RA) and a return towards normal function.

As used herein, "treatment" refers to a reduction of signs or symptoms, or to a reduction of side effects. Symptoms are "reduced" when the magnitude (e.g. intensity) or frequency of symptoms is reduced. In the case of RA, symptoms are reduced, for example, when the subject experiences less pain, a shorter duration of morning joint stiffness, and less swelling in the affected joints. It is not intended that the present disclosure be limited only to cases where the symptoms are eliminated. The present disclosure specifically contemplates treatment such that symptoms are reduced (and the condition of the subject is thereby "improved"), albeit not completely eliminated.

As used herein, "derivatives" or "analogues" of a peptide refers to a number of alterations in such peptides. In some embodiments, the derivatives comprise peptides with amino acid sequence changes. Such changes can be conservative amino acid substitutions amino acid deletions or amino acid insertions, provided that the shared epitope or shared epitope motif activity is substantially (50% or greater) retained. Analogues have amino acid analogues in place of the corresponding natural amino acids. Examples of such analogues include (but are not limited to) p-fluorophenylalanine (an analogue of phenylalanine) and ethionine and norleucine. Analogues also include incorporation of D-amino acids at particular points along the peptide chain. Derivatives and analogues may be conjugated.

As used herein "protease resistant peptides" refers to modified peptides with a reduced (e.g., relative to peptides without modification) susceptibility to protease digestion. For example, a protease resistant peptide may comprise a protecting group, or may comprise at least one D-amino acid. It is not intended that the present disclosure be limited to complete protease resistance. It is enough if susceptibility to protease digestion is reduced. In some embodiments, susceptibility to protease digestion is reduced, for example, 20%, 30%, 50%, 75%, 80%, 90% 95% or more relative to peptides without modification (e.g, as measured by an in vitro or in vivo protease assay).

As used herein, "synthetic peptide" refers to a peptide made by chemical or or in vitro enzymatic synthetic procedures. Synthetic shared epitope- and shared epitope motif-containing peptides, derivatives, analogues and mimetics are contemplated.

As used herein, "protecting groups" are those groups that prevent undesirable reactions (such as proteolysis) involving unprotected functional groups. Protecting groups can be added to the N-terminus, C-terminus or both of a shared epitope-containing or shared epitope motif-containing peptide. In one embodiment, the present disclosure contemplates that the protecting group is an acyl or an amide. In one embodiment, the acyl is acetate. In another embodiment, the protecting group is a benzyl group. In another embodiment, the protecting group is a benzoyl group. The present disclosure also contemplates combinations of such protecting groups.

As used herein, "biological activity" of peptides, derivatives or analogues, mimetics and antagonists refers to the ability of the peptides, derivatives or analogues, mimetics and antagonists (e.g., cyclic shared-eptiope antagonist peptides) to modulate signal transduction pathways or inhibit shared-epitope peptide activity. Such activity can be assayed by a number of techniques. For example, biological activity can be assayed in an in vitro cAMP-mediated assay for DNA repair following induction of DNA damage. Shared epitope-containing peptides inhibit DNA repair in such an assay. Biological activity of such peptides can also be determined by measuring intracellular cAMP levels or protein kinase A activation following application of said peptides to cells.

As used herein, the "N-terminus" of a peptide refers to the end of the peptide with a free amino group. Note that the N-terminus amino group does not necessarily have to be "free", for example, it may be involved in linking of moieties to the N-terminus in conjugates. As used herein, the "C-terminus" of a peptide refers to the end with a free carboxyl group. Note that the C-terminus carboxyl group does not necessarily have to be "free", for example, it may be involved in linking moieties to the C-terminus in conjugates.

As used herein, "single dosage" refers to a pharmaceutical composition of a formulation that is capable of achieving its intended effect in a single application or administration (e.g., once a day, once a week, or other interval).

As used herein, "oral administration" or "orally" refers to the introduction of a pharmaceutical composition into a subject by way of the oral cavity (e.g., in aqueous liquid or solid form).

As used herein, "sublingual administration" or "sublingually" refers to the introduction of a pharmaceutical composition into a subject by application to the mucosal surface under the tongue (within the oral cavity) such that the composition is absorbed into the subject.

As used herein, "buccal administration" or "buccal" refers to the introduction of a pharmaceutical composition into a subject by application to the mucosal surface lining the cheek (within the oral cavity) such that the composition is absorbed into the subject.

As used herein, "intranasal administration" or "intranasally" refers to the introduction of a pharmaceutical composition within the nasal cavity.

As used herein, "respiratory inhalation" refers to the introduction of a pharmaceutical composition within the respiratory tract.

As used herein, "intrapulmonary delivery" refers comprises administration to the lung. Intrapulmonary delivery of pharmacologic agents to patients can be accomplished via aerosolization. Alternatively, the agent may be administered to the lung through a bronchoscope.

As used herein, "transdermal administration" or "transdermally" or "cutaneously" refers to the introduction of a pharmaceutical composition into a subject by application to the surface of the skin such that the composition is absorbed into the subject.

As used herein, "injection" or "standard injection" refers to the placement of a pharmaceutical composition into a subject (e.g., with a hypodermic needle). For example, such injection can be made subcutaneously, intravenously, intramuscularly, intracavernosally, etc.

As used herein, "intra-articular" injection refers to direct injection of a pharmaceutical composition into a joint (for example, in a method of treatment of RA).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present disclosure. A "known therapeutic compound" refers to a therapeutic compound that has been shown (e.g., through animal trials or prior experience with administration to humans) to be effective in such treatment or prevention.

As used herein, the term "subject" refers to organisms to be treated by the methods of the present disclosure. Such organisms include, but are not limited to, mammals (e.g., murines, simians, equines, bovines, porcines, canines, felines, and the like), and most preferably includes humans. In the context of the disclosure, the term "subject" generally refers to an individual who will receive or who has received treatment (e.g., administration of a compound of the present disclosure and optionally one or more other agents) for a condition associated with an autoimmune disease (e.g., RA).

As used herein, the term "effective amount" refers to the amount of a compound (e.g., a compound of the present disclosure) sufficient to effect beneficial or desired results. An effective amount can be administered in one or more administrations, applications or dosages and is not limited intended to be limited to a particular formulation or administration route.

As used herein, the term "co-administration" refers to the administration of at least two agent(s) (e.g., a compound of the present disclosure) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant. As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

DESCRIPTION OF THE DISCLOSURE

The present disclosure relates to methods and compositions for treating disease related to disorders of bone remodeling. In particular, the present disclosure relates to compositions and methods for treating rheumatoid arthritis.

Osteoclast (OC)-mediated bone damage is a common, devastating outcome in rheumatoid arthritis (RA) (Bromley et al., 1984 Arthritis Rheum. 27: 857-863; Gravallese et al., 2000. Arthritis Rheum. 43: 250-258). Despite the advent of biologic agents, treating erosive RA remains a challenging endeavor, due to insufficient understanding of the mechanisms that specifically trigger RA disease onset and determine its severity. Most current and emerging drugs are targeted at generic immune-modulating pathways or inflammatory cytokines. As a result, drug failure and/or side effects are all too common.

While the pathogenesis of RA is not well understood, it has been long observed that the majority of RA patients carry HLA-DRB1 alleles coding a five amino acid sequence motif called the 'shared epitope' (SE) in the region 70-74 of the DRβ chain (Gregersen et al., 1987. Arthritis Rheum. 30: 1205-1213). The SE not only confers a higher risk for RA, but also increases the likelihood of developing a more severe disease. SE-coding HLA-DRB1 alleles are associated with earlier disease onset and more severe bone erosions (Gonzalez-Gay et al., 2002. Semin. Arthritis Rheum. 31: 355-360; Mattey et al., 2001. Arthritis Rheum. 44: 1529-1533; Plant et al., 1998 J. Rheumatol. 25: 417-426; Weyand et al., 1994. J. Lab. Clin. Med. 124: 335-338). Furthermore, there is evidence of gene-dose effect, where the extent of bone destruction in RA correlates positively with the number of SE-coding HLA-DRB1 alleles (Mattey et al., supra; Plant et al., supra; Weyand et al., supra).

SE functions as a signal transduction ligand that binds to cell surface calreticulin (CRT) in a strictly allele-specific manner and activates nitric oxide (NO)-mediated pro-oxidative signaling (Ling et al., 2006. Arthritis Rheum. 54: 3423-3432; Ling et al., 2007. Arthritis Res Ther 9: R5; Ling et al., 2007. The Journal of Immunology 179: 6359-6367; Ling et al., 2012 Arthritis Rheum.; De Almeida et al., 2010. The Journal of Immunology 185: 1927-1934; Holoshitz et al., 2010 Ann. N. Y. Acad. Sci. 1209: 91-98; U.S. Pat. Nos. 7,208,154; 7,074,893; each of which is herein incorporated by reference in its entirety). One of the functional consequences of SE ligand-activated signaling is expansion of IL-17-producing T (Th17) cells, both in vitro and in vivo (De Almeida et al., supra)).

Th17 cells are central players in arthritis pathogenesis (Shahrara et al., 2008 Arthritis Res Ther 10: R93). These cells have been previously shown to express high levels of the receptor activator for nuclear factor-KB (RANK) ligand (RANKL) and activate osteoclastogenesis (Sato et al., 2006 J. Exp. Med. 203: 2673-2682; Kotake et al., 1999 J. Clin. Invest. 103: 1345-1352). In previous studies, it was demonstrated that the SE ligand facilitates osteoclast (OC) differentiation in mouse and human cells in vitro and enhanced the differentiation of RAKL-expressing Th17 cells. When administered in vivo to mice with collagen-induced arthritis (CIA), the SE ligand increased joint swelling, synovial tissue OC abundance and erosive bone damage (Holoshitz et al., 2012, J. Immunol).

Given that the SE acts as a signal transduction ligand that directly contributes to arthritis severity, experiments described herein developed ways to inhibit this pathway. Experiments described herein describe the development of peptidomimetic SE-antagonistic ligands.

Targeting the SE-CRT pathway provides an additional advantage over the prevailing therapeutic paradigms, due to the unique role played by this pathway at an 'upstream' phase in RA pathogenesis. The SE is the single most significant risk factor for RA. It determines susceptibility, severity and even disease penetrance in monozygotic twins (Jawaheer et al., 1994 Arthritis Rheum. 37: 681-686). Thus, different from effector cytokines or enzymes involved in lymphocyte activation, this pathway is intimately involved in disease etiology and early genesis.

I. Compounds

As described herein, embodiments of the present disclosure provide cyclic SE peptides for use in research, screening, and therapeutic applications. In some embodiments, peptide are cyclic SE antagonist or inhibitor peptides. Provided herein are peptide mimetics that target the SE-activated pathway. In some embodiments, the compounds have the structure

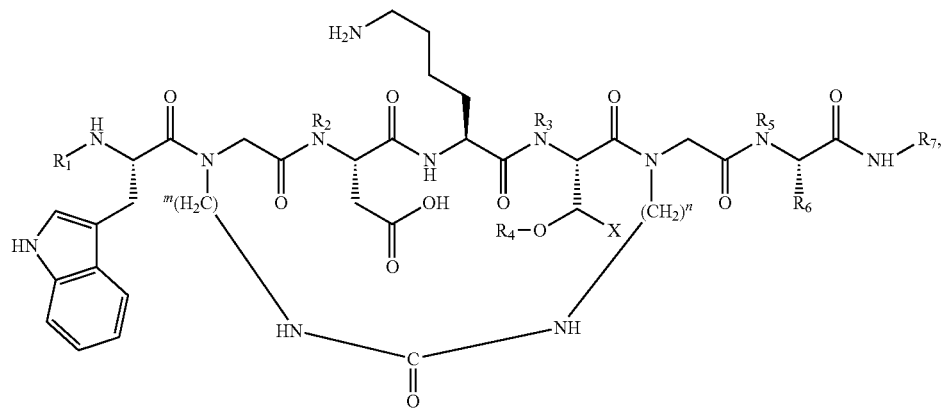

where m and n are the same or different and are integers between 1 and 4; X is H or $CH_3$; $R_1$ is H amidino, a glycosylated serine or threonine residue, or one or more arginine residues, $R_2$ is H or methyl, $R_3$ is H or methyl, $R_4$ is H or a β or α sugar (e.g., glucose, xylose, fucose, lactose, maltose, etc.), $R_5$ is H or methyl, $R_6$ is $CH_3$, OH, or O-β or α sugar (e.g., glucose, xylose, fucose, lactose, maltose, etc.), $R_7$ is H, a glycosylated serine or threonine residue, or one or more arginine residues.

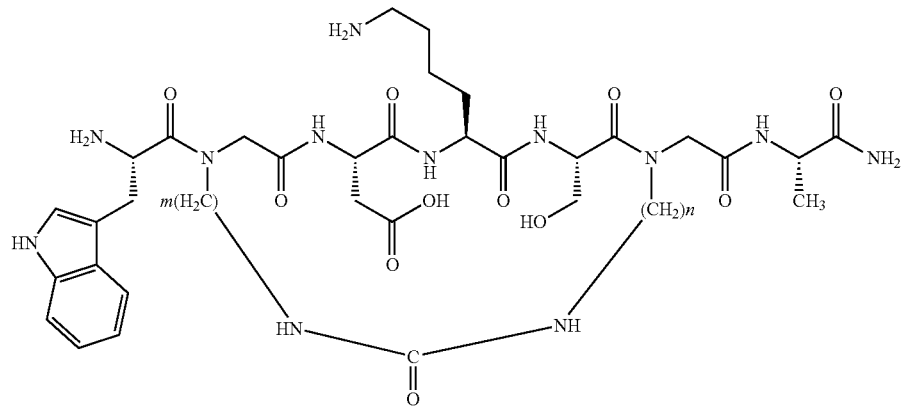

where m and n are integers between 1 and 4 (SEQ ID NO:1).
In some embodiments, the structure is:

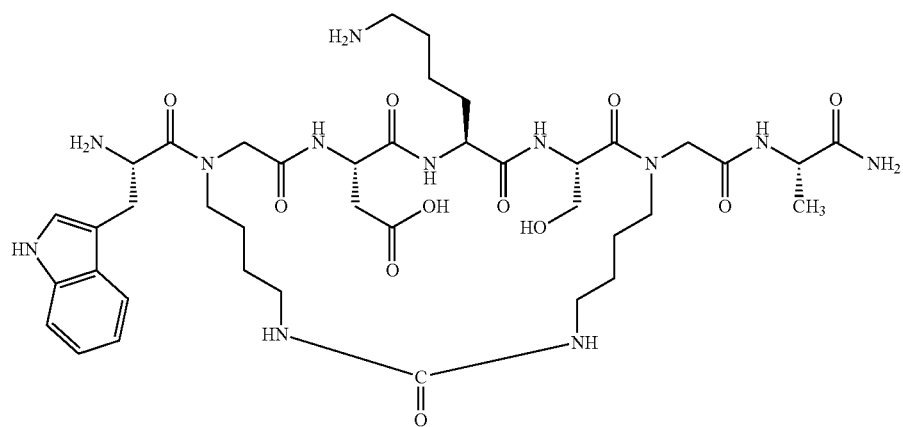 [SMILES: C[C@H](NC(=O)CN1CCCCNC(=O)NCCCCN(C(=O)[C@@H](N)Cc2c[nH]c3ccccc23)CC(=O)N[C@@H](CC(=O)O)C(=O)N[C@@H](CCCCN)C(=O)N[C@@H](CO)C1=O)C(N)=O]

(Trp-c[Gly(4-aminobutyl)-Asp-Lys-Ser-Gly(4-aminobutyl)]-Ala-NH2 (SEQ ID NO:1); FIG. 1).

In some embodiments, the structure is

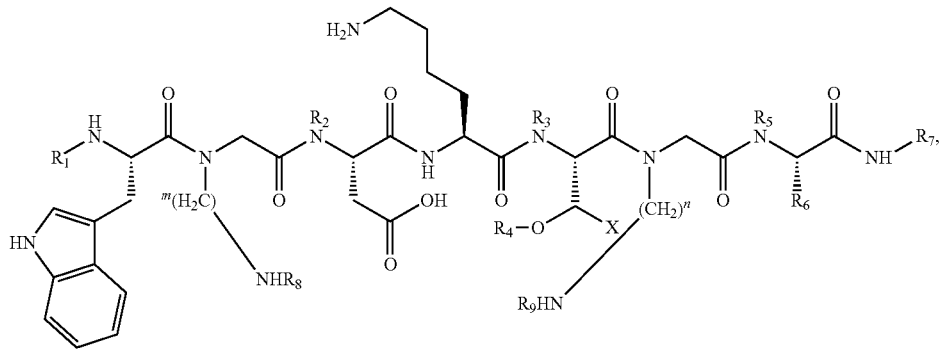

where m and n are the same or different and are integers between 1 and 4; X is H or $CH_3$; $R_1$ is H amidino, a glycosylated serine or threonine residue, or one or more arginine residues, $R_2$ is H or methyl, $R_3$ is H or methyl, $R_4$ is H or a β or α sugar (e.g., glucose, xylose, fucose, lactose, maltose, etc.), $R_5$ is H or methyl, $R_6$ is $CH_3$, OH, or O-β or α sugar (e.g., glucose, xylose, fucose, lactose, maltose, etc.), $R_7$ is H, a glycosylated serine or threonine residue, or one or more arginine residues, $R_8$ is H or acetyl, and $R_9$ is H or acetyl.

The present disclosure also provides methods of modifying and derivatizing the compositions of the present disclosure to increase desirable properties (e.g., binding affinity, activity, solubility and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In some embodiments, rational design methods are used to predict and model in silico ligand-receptor interactions prior to confirming results by routine experimentation.

In some embodiments, the present disclosure contemplates compounds that are protease resistant. In one embodiment, such protease-resistant peptides are peptides comprising protecting groups. In some embodiments, the present disclosure contemplates a peptide that is protected from protease degradation by N-terminal acetylation ("Ac") and C-terminal amidation. The acetylated and amidated shared epitope- or shared epitope motif-containing peptide is useful for in vivo administration because of its resistance to proteolysis.

In another embodiment, the present disclosure also contemplates peptides comprising their corresponding D-isomers. It is not intended that the present disclosure be limited to particular amino acids and particular D-isomers. This embodiment is feasible for all amino acids, except glycine; that is to say, it is feasible for all amino acids that have two stereoisomeric forms. By convention, these mirror-image structures are called the D and L forms of the amino acid. These forms cannot be interconverted without breaking a chemical bond. With rare exceptions, only the L forms of amino acids are found in naturally occurring proteins.

In other embodiments, peptides protected from protease degradation by both the use of protecting groups and substitution of L-amino acids with their corresponding D-isomers are contemplated. For example, a peptide comprising at least one D-amino acid can be acetylated and amidated as described above.

Synthesis of non-peptide compounds that mimic peptide sequences is also known in the art. Eldred et al. (J. Med. Chem. 37:3882 (1994)) describe non-peptide antagonists that mimic an Arg-Gly-Asp sequence. Likewise, Ku et al. (J. Med. Chem. 38:9 (1995)) give further elucidation of a series of such compounds. Such non-peptide compounds that mimic the compounds described herein are specifically contemplated.

The present disclosure also contemplates synthetic mimicking compounds that are multimeric compounds that repeat the relevant peptide sequences.

The present disclosure contemplates the design of peptide and nonpeptide mimetics based upon structural modeling of the compounds described herein, high resolution experimental three dimensional imaging of the compounds, conformational and binding site analysis of shared epitope- and calreticulin-inhibitory peptides, rational design of shared epitope- and calreticulin-inhibitory compounds, screening of combinatorial peptide libraries for shared epitope- and calreticulin-inhibitory constituents, and design of bio-stable shared epitope- and calreticulin-inhibitory peptide and non-peptide mimetics. Certain of the compounds suitable for use in the present disclosure may exist as stereoisomers including optical isomers. The disclosure includes all stereoisomers and both the racemic mixtures of such stereoisomers as well as the individual enantiomers that may be separated according to methods that are well known to those of skill in the art. In certain embodiments, the compounds of the present disclosure do not comprise more than three naturally occurring amino acids, preferably no more than two naturally occurring amino acids, even more preferably no more than one naturally occurring amino acid.

Conjugates comprising the shared peptides described herein or analogues, derivatives, or mimetics linked to at least one additional moiety are also contemplated. The additional moiety may be a carrier molecule, to facilitate delivery of the conjugate to the appropriate target organ or tissue. In some embodiments, the conjugates are contemplated for delivery to the brain, for example, across the blood brain barrier. In other embodiments, the conjugates are contemplated for enhanced permeability for topical administration (for example, topical administration over a joint affected by rheumatoid arthritis).

A variety of carrier molecules are contemplated, and may vary, depending on the desired delivery or administration format. Among the carrier molecules contemplated are lipophilic or hydrophobic moieties, antibodies (and fragments thereof) and polyamines, although additional carrier molecules are also considered.

The present disclosure is not limited by the method of introduction of the therapeutic compound to the body. Among other methods, the present disclosure contemplates administering cutaneously, orally, or by standard injection (e.g. intravenous).

The present disclosure also contemplates administering the compounds described herein, derivatives, mimetics, conjugates or antagonists to the patient intranasally or through respiratory inhalation. Formulations suitable for intranasal administration include ointments, creams, lotions, pastes, gels, sprays, aerosols, oils and other pharmaceutical carriers which accomplish direct contact between the compounds of the disclosure or a pharmaceutical composition comprising compounds of the disclosure and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all herein incorporated by reference. Formulations suitable for respiratory inhalation include ointments, creams, lotions, pastes, gels, sprays, aerosols, oils and other pharmaceutical carriers which accomplish direct contact between compounds of the disclosure or a pharmaceutical composition comprising compounds of the disclosure and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all herein incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to patients can be accomplished via aerosolization. Alternatively, the agent may be administered to the lung through a bronchoscope. Of course, the therapeutic agents may be investigated for their efficacy via other routes of administration, including parenteral administration.

While the present disclosure is not limited by the form of oral administration, aqueous and organic solutions of the compounds described herein, derivatives, mimetics, conjugates or antagonists are contemplated. Likewise, compounds of the disclosure can be associated with a solid pharmaceutical carrier for solid oral administration (e.g., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

The compounds described herein, derivatives, mimetics, conjugates or antagonists may also be administered cutaneously in a carrier adapted for topical administration. Such carriers include creams, ointments, lotions, pastes, jellies, sprays, aerosols, bath oils, or other pharmaceutical carriers that accomplish direct contact between the compounds of the disclosure and the pore of the skin. In general pharmaceutical preparations may comprise from about 0.001% to about 10%, and preferably from about 0.01 to 5% by w/w of the active compound. In some cases it may be useful to dissolve the active compound in an appropriate solvent such as ethanol or DMSO (dimethylsulfoxide), and the like, to facilitate incorporation into a pharmaceutical preparation.

While the present disclosure is not limited by a specific method of introducing compounds of the disclosure by injection, injection of the compounds of the disclosure can be carried out by any conventional injection means (e.g., employing an hypodermic syringe and needle or a similar device such as the NovolinPen. sold by Squibb-Novo, Inc., Princeton, N.J., USA). This injection may be by the subject injecting him or herself or by another person injecting the patient.

The compounds described herein, derivatives, mimetics, conjugates or antagonists can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate buffered saline, in which compounds of embodiments of the present disclosure are dissolved or suspended, such that the resulting composition is suitable for injection. Such a physiologically acceptable composition can also include a nonirritant preservative, such as, e.g., benzalkonium chloride at 0.05% (w/v) to 0/2% (w/v).

While the present disclosure is not limited to the method of injecting compounds, in some embodiments, it is injected with a standard syringe. One skilled in the art would be capable of injecting compounds of the present disclosure with a carrier as described above.

In some embodiments (e.g. in a method of treating a subject with symptoms of RA), it is desirable that the compositions of the disclosure reach the affected joints. In some embodiments, this may be accomplished by cutaneous or transdermal application of pharmaceutical compositions comprising the compounds described herein, derivatives, mimetics, conjugates or antagonists directly to the skin over the affected joint. In other embodiments, delivery of the compounds to the affected joints may be by direct injection into the joint. The present disclosure specifically contemplates intra-articular injections in RA patients.

To perform an arthrocentesis, the specific area of the joint to be injected is palpated and is then marked, e.g., with firm pressure by a ballpoint pen that has the inked portion retracted. This will leave an impression that will last 10 to 30 minutes. (The ballpoint pen technique can also be used with soft tissue injection.) The area to be aspirated and/or injected should be carefully cleansed with a good antiseptic, such as one of the iodinated compounds. Then the needle can be inserted through the ballpoint pen impression.

Helpful equipment includes the following items: alcohol sponges; iodinated solution and surgical soap; gauze dressings (2×2); sterile disposable 3-, 10- and 20-ml syringes; 18- and 20-gauge, 1½-inch needles; 20-gauge spinal needles; 25-gauge, ⅝-inch needles; plain test tubes; heparinized tubes; clean microscope slides and coverslips; heparin to add to heparinized tubes if a large amount of inflammatory fluid is to be placed in the tube; fingernail polish to seal wet preparation; chocolate agar plates or Thayer-Martin medium; tryptic soy broth for most bacteria; anaerobic transport medium (replace periodically to keep culture media from becoming outdated); tubes with fluoride for glucose; plastic adhesive bandages; ethyl chloride; hemostat; tourniquet for drawing of simultaneous blood samples; and 1 percent lidocaine.

Knee.

The knee is the easiest joint to inject. The patient should be in a supine position with the knee fully extended. The puncture mark is made just posterior to the medial portion of the patella, and an 18- to 20-gauge, 1½-inch needle directed slightly posteriorly and slightly inferiorly. The joint space should be entered readily. On occasion thickened synovium or villous projections may occlude the opening of the needle, and it may be necessary to rotate the needle to facilitate aspiration of the knee when using the medial approach. An infrapatellar plica, a vestigal structure that is also called the ligamentum mucosum, may prevent adequate aspiration of the knee when the medial approach is used. However, the plica should not adversely affect injections or aspirations from the lateral aspect.

Shoulder.

Injections in the shoulder are most easily accomplished with the patient sitting and the shoulder externally rotated. A mark is made just medial to the head of the humerus and slightly inferiorly and laterally to the coracoid process. A 20- to 22-gauge, 1½-inch needle is directed posteriorly and slightly superiorly and laterally. One should be able to feel the needle enter the joint space. If bone is hit, the operator should pull back and redirect the needle at a slightly different angle.

The acromioclavicular joint may be palpated as a groove at the lateral end of the clavicle just medial to the shoulder. A mark is made, and a 22- to 25-gauge, ⅝- to 1-inch needle is carefully directed inferiorly. Rarely is synovial fluid obtained.

The sternoclavicular joint is most easily entered from a point directly anterior to the joint. Caution is necessary to avoid a pneumotharax. The space is fibrocartilaginous, and rarely can fluid be aspirated.

Ankle Joint.

For injections of the compounds of the present disclosure in the ankle joints, the patient should be supine and the leg-foot angle at 90 degrees. A mark is made just medical to the tibialis anterior tendon and lateral to the medial malleolus. A 20- to 22-gauge, 1½-inch needle is directed posteriorly and should enter the joint space easily without striking bone.

Subtalar Ankle Joint.

Again, the patient is supine and the leg-foot angle at 90 degrees. A mark is made just inferior to the tip of the lateral mallcolus. A 20- to 22-gauge, 1½-inch needle is directed perpendicular to the mark. With this joint the needle may not enter the first time, and another attempt or two may be necessary. Because of this and the associated pain, local anesthesia may be helpful.

Wrist.

This is a complex joint, but fortunately most of the intercarpal spaces communicate. A mark is made just distal to the radius and just ulnar to the so-called anatomic snuff box. Usually a 24- to 26-gauge, ⅝ to 1-inch needle is adequate, and the injection is made perpendicular to the mark. If bone is hit, the needle should be pulled back and slightly redirected toward the thumb.

First Carpometacarpal Joint.

Degenerative arthritis often involves this joint. Frequently the joint space is quite narrowed, and injections may be difficult and painful. A few simple maneuvers may make the injection fairly easy, however. The thumb is flexed across the palm toward the tip of the fifth finger. A mark is made at the base of the first metacarpal bone away from the border of the snuff box. A 22- to 26-gauge, ⅝ to 1-inch needle is inserted at the mark and directed toward the proximal end of the fourth metacarpal. This approach avoids hitting the radial artery.

Metacarpophalalangeal Joints and Finger Interphalangral Joints.

Synovitis in these joints usually causes the synovium to bulge dorsally, and a 24- to 26-gauge, ½ to ⅝-inch needle can be inserted on the either side just under the extensor tendon mechanism. It is not necessary for the needle to be interposed between the articular surfaces. Some prefer having the fingers slightly flexed when injecting the metacarpophalangeal joints. It is unusual to obtain synovial fluid. When injecting, a mix of the compounds of the present disclosure with a small amount of local anesthetic is also contemplated.

Metatarsophalangeal Joints and Toe Interphalangeal Joints.

The techniques are quite similar to those of the metacarpophalangeal and finger interphalangeal joints, but many prefer to inject more dorsally and laterally to the extensor tendons. Marking the area(s) to be injected is helpful as is gentle traction on the toe of each joint that is injected.

Elbow.

A technique preferred by many is to have the elbow flexed at 90 degrees. The joint capsule will bulge if there is inflammation. A mark is made just below the lateral epicondyle of the humerus. A 22-gauge, 1 to 1½-inch is inserted at the mark and directed parallel to the shaft of the radius or directed perpendicular to the skin.

Hip.

This is a very difficult joint to inject even when using a fluoroscope as a guide. Rarely is the physician quite sure that the joint has been entered; synovial fluid is rarely obtained. Two approaches can be used, anterior or lateral. A 20-gauge, 3½-inch spinal needle should be used for both approaches.

For the anterior approach, the patient is supine and the extremity fully extended and externally rotated. A mark should be made about 2 to 3 cm below the anterior superior iliac spine and 2 to 3 cm lateral to the femoral pulse. The needle is inserted at a 60 degree angle to the skin and directed posteriorly and medially until bone is hit. The needle is withdrawn slightly, and possibly a drop or two of synovial fluid can be obtained, indicating entry into the joint space.

Many prefer the lateral approach because the needle can "follow" the femoral neck into the joint. The patient is supine, and the hips should be internally rotated—the knees apart and toes touching. A mark is made just anterior to the greater trochanter, and the needle is inserted and directed medially and sightly cephalad toward a point slightly below the middle of the inguinal ligament. One may feel the tip of the needle slide into the joint.

Temporomandibular Joint.

For injections, the temporomandibular joint is palpated as a depression just below the zygomatic arch and 1 to 2 cm anterior to the tragus. The depression is more easily palpated by having the patient open and close the mouth. A mark is made and, with the patient's mouth open, a 22-gauge, ½ to 1-inch needle is inserted perpendicular to the skin and directed slightly posteriorly and superiorly.

II. Methods of Treatment

Embodiments of the present disclosure provide compositions and methods for treating a variety of autoimmune disease, including but not limited to, rheumatoid arthritis (RA). In some embodiments, compounds (e.g., the compounds described herein, derivatives, mimetics, conjugates or antagonists) are administered to subjects diagnosed with RA. In some embodiments, the administration reduces or eliminates one or more symptoms of RA. In some embodiments, administration prevents or reverses bone damage caused by RA.

In some embodiments, compositions comprising the compounds described herein, derivatives, mimetics, conjugates or antagonists are administered once to an subject in need thereof. In other embodiments, compositions are administered on an ongoing, recurrent, or repeat basis (e.g., multiple times a day, once a day, once every 2, 3, 4, 5, or 6 days, once a week, etc.) for a period of time (e.g., multiple days, months, or weeks). Suitable dosages and dosing schedules are determined by one of skill in the art using suitable methods (e.g., those described in the experimental section below or known to one of skill in the art).

In some embodiments, the present disclosure provides methods of treating disorder characterized as involving deregulated bone remodeling. Examples include, but are not limited to, inflammatory, metabolic, pharmacologic endocrinologic, infectious, neopleastic, mecahnical and idiopathic diseases. The following are representative examples for the above-mentioned categories:

Inflammatory: arthritis (e.g., rheumatoid arthritis), periodontal disease, psoriatic arthritis, reactive arthritis, gout, SLE, ankylosing spondylitic, osteoarthritis, etc.

Metabolic: Osteoporosis, anorexia nervosa

Endocinologic: vitamin D deficiency, Cushing's syndrome, hyperparathyroidism

Pharmacologic: Corticosteroids, other drug-induced osteoporosis

Infectious: osteomyelitis

Neoplastic: Bone metastasis, primary bone tumors, multiple myeloma, etc.

Mechanical: bone fracture healing, post-surgical, prosthesis-associated bone damage, disuse, paralysis, bedridden conditions, low gravity, etc.

Idiopathic: Paget's disease of bone, osteonecrosis

EXPERIMENTAL

The following examples serve to illustrate certain preferred embodiments and aspects of the present disclosure and are not to be construed as limiting the scope thereof.

Example 1

FIG. 1 shows BK2. BK2 is heptapeptide that contains two ε-amino N-butylglycine residues cyclized via a urea function. BK2 was synthesized in 3 steps. First, linear protected peptide ZTrp(Boc)-(4-Boc)-aminobutyl-Gly-Asp (OtBu)-Lys(Z)-Ser(OtBu)-(4-Boc)-aminobutyl-Gly-Ala-NH2 was synthesized using microwave-assisted protocols on a solid support (Rink resin). HOAt/HATU/DIEA was used for couplings and 20% piperidine or 5% piperazine for removal of Fmoc-protection. The linear peptide was cleaved and deprotected using a mixture of TFA:TIS:D.I. water (9.5:0.25:0.25) and subsequently purified using HPLC. Backbone urea cyclization of the partially protected linear peptide was done using bis(4-nitrophenyl)carbonate (Filip et al., *Journal of Peptide Science.* 9: 649-657, 2003). The cyclic peptide was purified and subjected to hydrogenolysis in the presence of Pd/BaSO4 in order to remove the carbobenzyloxy groups from Trp and Lys residue. The final target peptide was purified and analyzed by HPLC and LC-MS.

Synthesis of the Ser(Glc)5-analog of BK2 included one additional step, the removal of the acetyl groups from the protected glucose moiety. This was accomplished by treating the peptide resin with a 4:1 mixture of hydrazine monohydrate:methanol for 1.5 hour.

Figure 2:
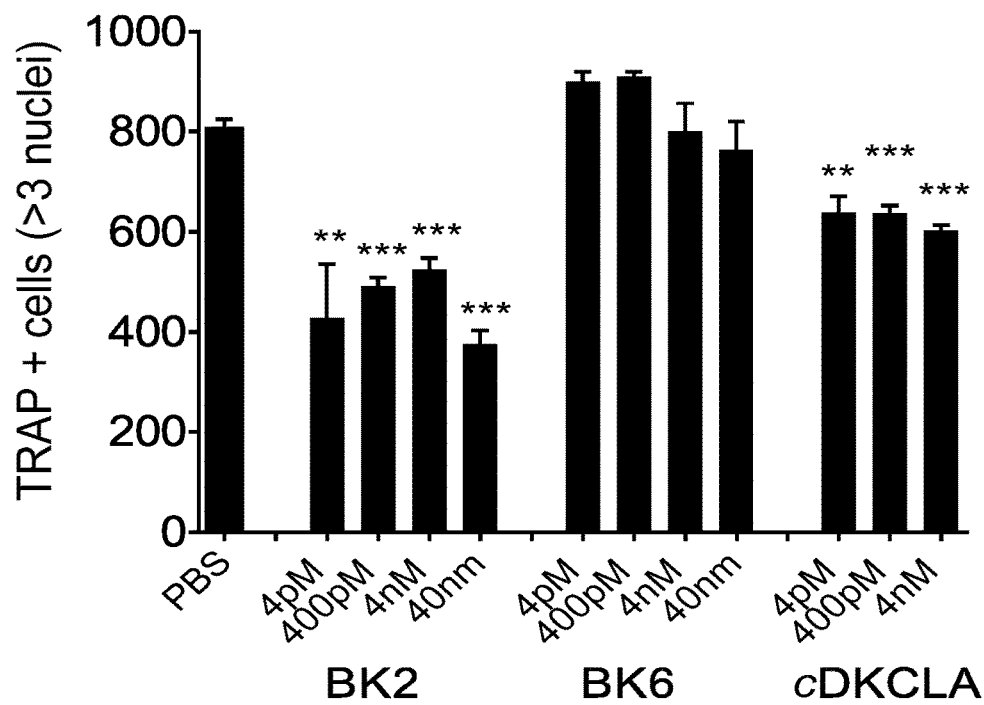
FIG. 2 shows anti-osteoclastogenic and effect of BK. In vitro osteoclastogenesis of murine pre-OC cell line RAW 264.7 in the presence of different doses of BK2. A negative control analog, BK6 fails to inhibit.
Figure 3:
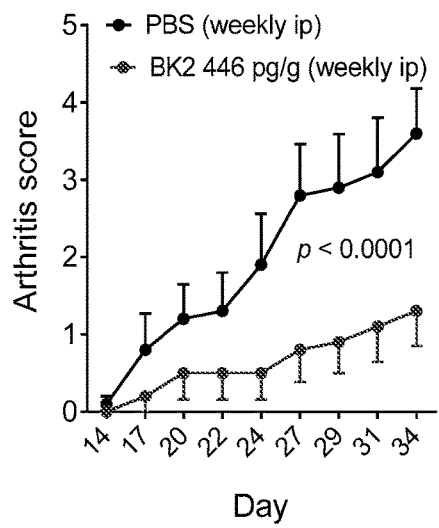
FIG. 3 shows anti-arthritogenic effects of BK2. A. DBA/1 mice with CIA received weekly ip doses of BK2, 446 pg/gm, or PBS (black) starting on day −1 relative to day of CIA induction, and joint swelling was recorded. N=10 per group. B. DBA/1 mice with CIA received a total of 4 weekly ip doses of BK2, 446 pg/gm, or PBS (black) starting at day 20 relative to day of CIA induction, at the time of arthritis onset, and joint swelling was recorded. Arrows indicate the treatment days. N=10 per group. C. DBA/1 mice with CIA received weekly sq doses of BK2446 pg/gm, or PBS (black) starting at day −1 relative to day of CIA induction, and joint swelling was recorded. N=10 per group. D. Radiological scores reveal protective effect on bone destruction by BK2. E. DBA/1 mice with CIA received a total of 4 weekly sq doses of BK2, 446 pg/gm, or PBS (black) starting at day 20 relative to day of CIA induction, at the time of arthritis onset, and joint swelling was recorded. Arrows indicate the treatment days. N=10 per group. F. Radiological scores reveal protective effect on bone destruction by BK2.
Figure 3:
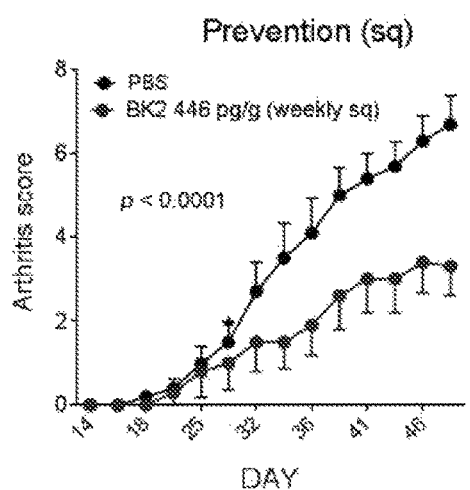
Figure 3:
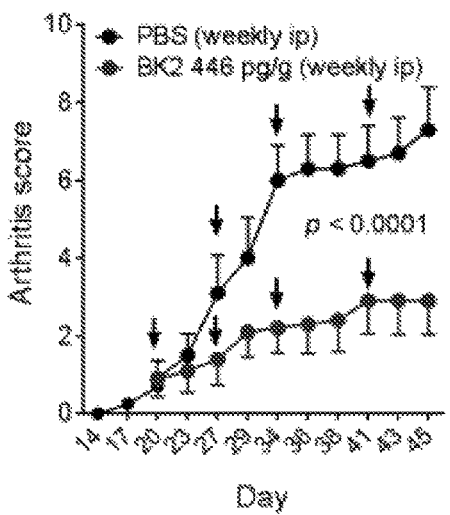
Figure 3:
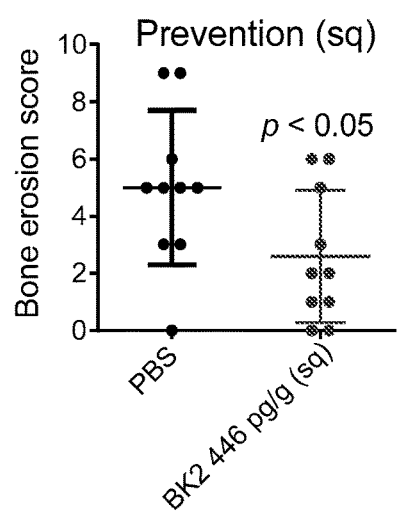
Figure 3:
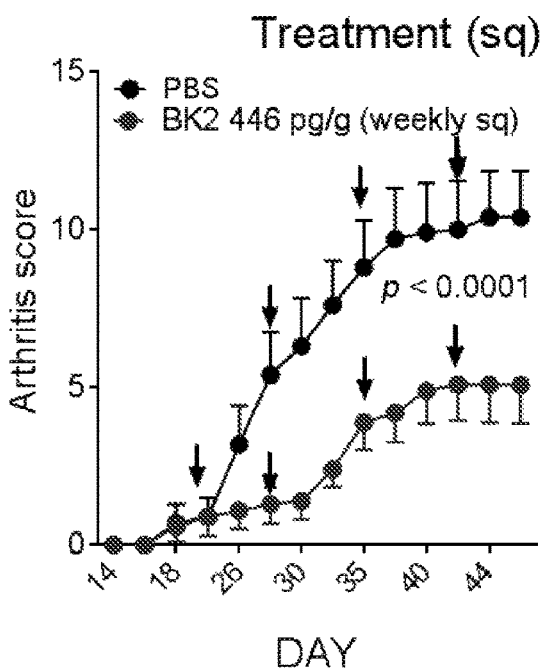
Figure 3:
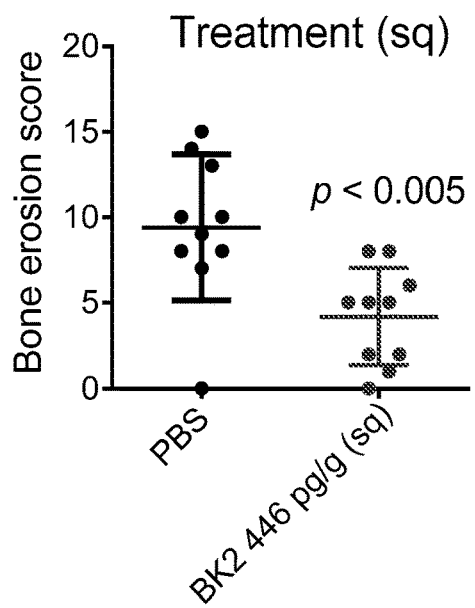

In vitro experiments demonstrate that BK2: 1. Is a potent inhibitor of SE-activated signaling ($IC_{50}$~$10^{-2}$ M); 2. Has pM-range $IC_{50}$ of anti-osteoclastogenic effect in vitro (mouse and human cells—FIG. 2); 3. Exerts a highly potent (picogram-range doses) inhibition effect on CIA (FIGS. 3A, 3B, 3C, 3E), as well as osteoclastogenesis and bone destruction in vivo (FIGS. 3D, 3F).

Example 2

In some embodiments, modified versions of BK2 are prepared. In some embodiments, glycosylation via the side chain β-hydroxyl of serine is employed. Several approaches for glycosylation of BK2 may be utilized. Since BK2 contains a Ser as residue 5, this is the first location for glycosylation. In addition, replacement of the C-terminal Ala of BK2 with glycosylated serine and the extension of BK2 by adding a C-terminal or N-terminal glycosylated Ser to form an octapeptide may be made. Typically glycosylation utilizes β-glucose, although other mono- and disaccharides can be employed.

In some embodiments, N-methylation of amino acids within a peptide sequence is employed. BK2 has several residues that can be replaced by the corresponding N-Me amino acid: $Trp^1$, $Asp^3$, $Lys^4$, $Ser^5$, and $Ala^7$. These replacements are incorporated individually and in combinations. N-methyl analogs of all these amino acids, suitably protected for peptide synthesis are commercially available.

In some embodiments, amidination of N-terminal amino acids in a peptide sequence is employed. The N-terminal Trp α-amine of BK2 is amidinated.

In parallel with the modifications described above, several modifications to the cyclic scaffold may be employed. In particular, the effect of replacing N-aminobutylglycine, urea cyclization with a hydrocarbon staple is contemplated. In this approach, amino acids with olefin containing hydrocarbon side chains are cyclized using a ruthenium catalyzed ring closing metathesis to form an all hydrocarbon cross link. Cyclization is typically between n and n+4 resides (as is suitable for a BK2 analog) and is employed by replacement of the N-aminobutylglycine residues 2 and 6 of BK2. In some embodiments, analogous linear analogs may be made using combinations of N-butylglycine, N-aminobutylglycine, and ε-acetyl-N-aminoglycine at resides in 2 and 6.

Analogs may be tested using assays described, for example, in WO 2014/130949; herein incorporated by reference in its entirety.

Having fully described the disclosure, it will be understood by those of skill in the art that the same can be performed within a wide and equivalent range of conditions, formulations, and other parameters without affecting the scope of the disclosure or any embodiment thereof. All patents, patent applications and publications cited herein are fully incorporated by reference herein in their entirety.

We claim:

1. A composition comprising a compound having the structure:

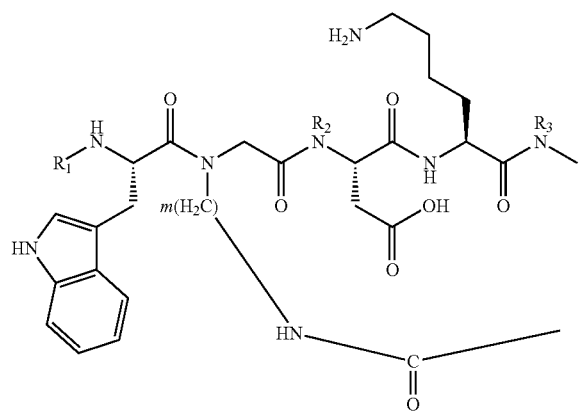

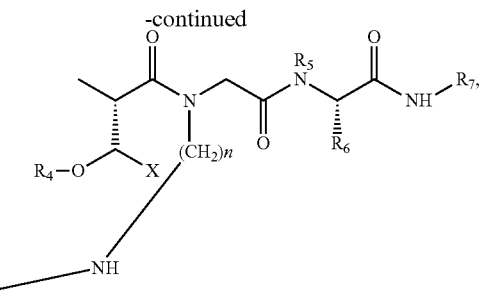

where m and n are the same or different and are integers between 1 and 4; X is H or $CH_3$; $R_1$ is H, —C(=NH)$NH_2$, a glycosylated serine or threonine residue, or one or more arginine residues; $R_2$ is H or methyl; $R_3$ is H or methyl; $R_4$ is H or a β or α sugar; $R_5$ is H or methyl; $R_6$ is $CH_3$, OH, or O-β or α sugar; and $R_7$ is H, a glycosylated serine or threonine residue, or one or more arginine residues.

2. The composition of claim 1, wherein said compound has the structure:

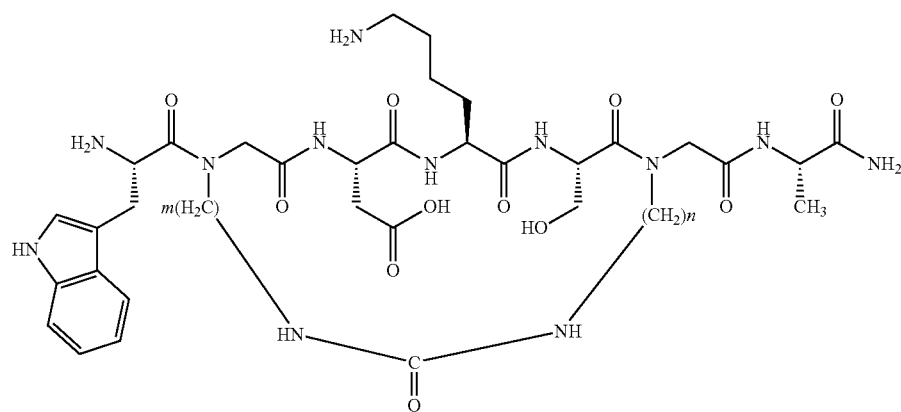

(SEQ ID NO:1) where m and n are integers between 1 and 4.

3. The composition of claim 2, wherein said compound has the structure:

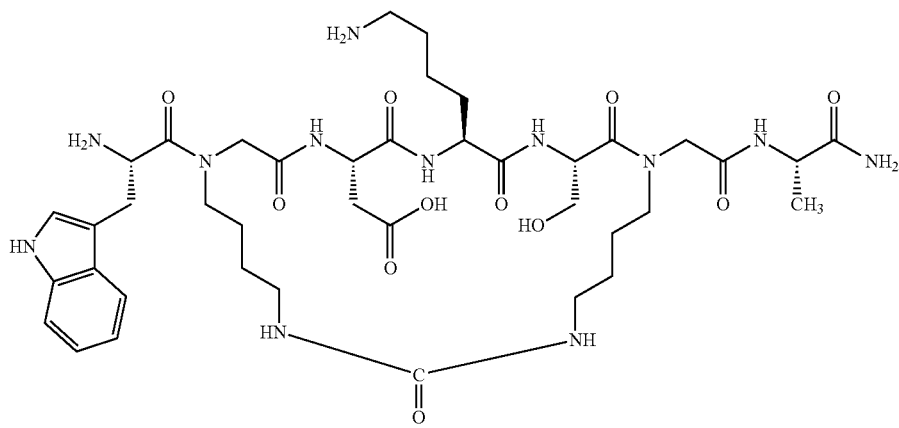 [SMILES: C[C@H](NC(=O)CN1CCCCNC(=O)NCCCCN(C(=O)[C@@H](N)Cc2c[nH]c3ccccc23)CC(=O)N[C@@H](CC(=O)O)C(=O)N[C@@H](CCCCN)C(=O)N[C@@H](CO)C1=O)C(N)=O]

(Trp-c[Gly(4-aminobutyl)-Asp-Lys-Ser-Gly(4-aminobutyl)]-Ala-NH$_2$) (SEQ ID NO:1).

4. A composition comprising a compound having the structure:

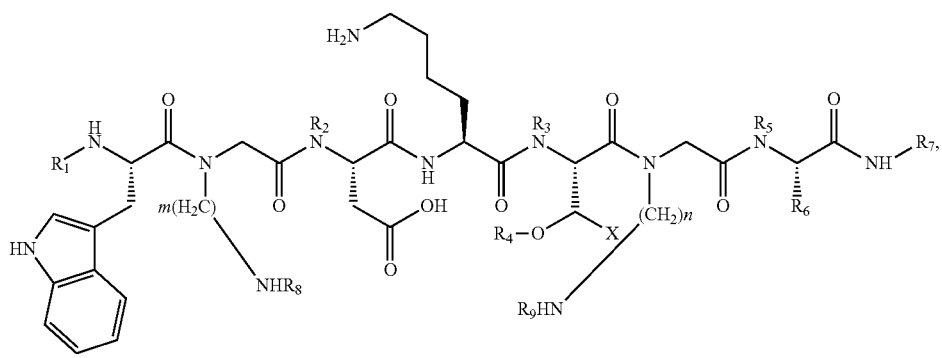

where m and n are the same or different and are integers between 1 and 4; X is H or CH$_3$; R$_1$ is H, —C(=NH)NH$_2$, a glycosylated serine or threonine residue, or one or more arginine residues; R$_2$ is H or methyl; R$_3$ is H or methyl; R$_4$ is H or a β or α sugar; R$_5$ is H or methyl; R$_6$ is CH$_3$, OH, or O-β or α sugar; R$_7$ is H, a glycosylated serine or threonine residue, or one or more arginine residues; R$_8$ is H or acetyl; and R$_9$ is H or acetyl.

5. The composition of claim 1, wherein said β or α sugar is selected from the group consisting of glucose, xylose, fucose, lactose, and maltose.

6. The composition of claim 1, wherein R$_4$ is a β or α sugar.

7. The composition of claim 1, wherein R$_6$ is an O-β or α sugar.

8. The composition of claim 7, wherein R$_6$ comprises β-glucose.

9. The composition of claim 1, wherein one or more amino acids of said composition comprising an R$_2$, R$_3$, or R$_5$ group are N-methylated.

10. The composition of claim 1, wherein the N-terminal Tryptophan amino acid of said composition is amidinated at the —NH$_2$ group.

11. The composition of claim 1, wherein said composition is a pharmaceutical composition.

12. The composition of claim 11, wherein said composition comprises a pharmaceutically acceptable carrier.

13. A method of treating or preventing a bone remodeling disorder, comprising administering a composition of claim 1 to a subject.

14. The method of claim 13, wherein said subject has been diagnosed with a bone remodeling disorder.

15. The method of claim 14, wherein said bone remodeling disorder is bone destruction from rheumatoid arthritis.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Artificial sequence
<220> FEATURE:
<223> OTHER INFORMATION: Synthetic

<400> SEQUENCE: 1

Trp Gly Asp Lys Ser Gly Ala
1               5